United States Patent [19]

Fust

[11] Patent Number: 6,083,525

[45] Date of Patent: Jul. 4, 2000

[54] COMPOSITIONS FOR FRESHENING NOSTRILS AND SINUS CAVITIES

[76] Inventor: Charles A. Fust, 3828 Chaumont Cir., Ocean Springs, Miss. 39564

[21] Appl. No.: 09/152,151

[22] Filed: Sep. 11, 1998

Related U.S. Application Data

[63] Continuation-in-part of application No. 09/123,646, Jul. 28, 1998, abandoned, which is a continuation-in-part of application No. 08/644,225, May 10, 1996, Pat. No. 5,785,988.

[51] Int. Cl.⁷ ..................................................... G03B 7/08
[52] U.S. Cl. ........................................... 424/435; 424/435
[58] Field of Search ...................................... 424/434, 435

[56] References Cited

U.S. PATENT DOCUMENTS 5,622,992   4/1997   Beck ........................................ 514/613

*Primary Examiner*—Carlos A. Azpuru
*Attorney, Agent, or Firm*—James W. Kayden; Thomas, Kayden, Horstemeyer & Risley

[57] ABSTRACT

A composition for freshening sinus cavities including a carrier for a masking agent that conceals and eliminates odors emanating from the sinus cavities, and further including an anti-septic or anti-infective constituent. The composition may further include a moisturizing base component, a preservative, a counter irritant, and an alcohol.

7 Claims, No Drawings

COMPOSITIONS FOR FRESHENING NOSTRILS AND SINUS CAVITIES

This application is a CIP of U.S. Ser. No. 09/123,646 filed Jul. 28, 1998, now abandoned, which is a CIP of Ser. No. 08/644,225 filed May 10, 1996, now U.S. Pat. No. 5,785,988.

FIELD OF THE INVENTION

This invention relates to a composition that is applied to a person's nostrils and sinus cavities, using an inhaler or other suitable means, for freshening and deodorizing the named areas for controlling halitosis.

BACKGROUND OF THE INVENTION

Conventional control of halitosis or "bad breath", as it is often termed, is presently accomplished through the use of mouthwashes, breath mints, candy, chewing gum, brushing and flossing teeth, and other such means that are taken by mouth. Recent developments in this field have focused on the theory that the digestive organs can be responsible for objectionable odors that are produced from consuming certain foods or liquids.

Mouthwash rinses are used to flush the mouth with bacteria killing agents and, in most cases, with additives of various types designed to freshen the mouth and mask odors. Bacterial elimination is normally accomplished by the use of alcohol and/or various dilutions of saline solution. The use of alcohol in these products often causes the intrusive effect experienced by many persons as a burning sensation. Saline solutions are very effective bacteria killing agents and do not cause the burning sensation; however, the taste is not well received by most consumers. While effective in many cases, mouthwashes and other oral means of controlling breath odors can be supplemented with the composition that is the subject matter of the present invention.

SUMMARY OF THE INVENTION

It is, therefore, one of the principal objects of the present invention to freshen breath and eliminate or mask objectionable breath odors by introducing the present invention into the nostrils and therethrough, into the sinus cavities.

Another object of the present invention is to provide a composition which may be conveniently introduced through the nose with, for example, an inhaler or atomizer-type container and which causes no discomfort to the user.

A further object of the present invention is to provide an effective means of breath odor control as a substitute or supplement to conventional therapies and which has both immediate and residual effect.

These and additional objects are attained by the present invention which, in the broadest sense, comprises a carrier means, such as water or a dilute saline solution, and an odor masking agent. The odor masking agent can be an essential oil or flavoring means such as those used in conventional mouthwashes. Other additives may include a small quantity of alcohol for acting on bacteria and an adherent means such as glycerine for maintaining the composition in place in the nostrils and sinus cavities for a sufficient length of time to produce the desired effect. Other means such as preserving agents may also be employed.

Various additional objects and advantages of the present invention will become apparent from the following detailed description.

DETAILED DESCRIPTION OF THE PREFERRED EMBODIMENT

The present invention is a liquid composition that is inhaled through the nostrils and into the sinus cavities. It is of particular utility for use by persons who smoke cigarettes, cigars and the like as the smoke necessarily invades the nostrils and sinus cavities when it is inhaled.

The composition includes a carrier means, which can be water or a mild or dilute saline solution. The saline solution is preferred and provides a mild antibacterial effect. Saline solutions are also commonly used as moisturizers at present and are safely used in the nasal passages and sinuses. While the concentration may vary between 50% and 75%, a solution of 65% saline has been found to be effective and non-objectionable for the user.

Control and/or elimination of objectionable odors is accomplished using masking agents such as oil of peppermint, spearmint, etc., or agents having a fruity or citrus essence. Other agents include, but are not limited to eucalyptol, methyl salicylate, and various other flavoring means.

A small quantity of alcohol may be used to provide an antibacterial effect. The alcohol is not necessary but may facilitate mixing of the other components. A further component which may be added is a preserving agent such as benzalkonium chloride which is used to extend shelf life. The use of the preserving agent or agents depends on whether or not some or any of the other components are stable in storage.

The delivery method used for the present composition can vary, with spray bottles, droppers, and/or atomizer-type squeeze or pump bottles, all being suitable, among other delivery means. Experimentation with a one-half ounce (½ oz.) pump atomizer spray bottle proved to be an effective delivery means. Containers of this type are currently used by several pharmaceutical companies for introducing sinus medication into the nostrils and sinus cavities. The atomizer-type bottles reduce the contents of the bottle to a very fine mist, thus making the delivery of the composition minimally intrusive.

No discomfort for the user was experienced in testing of the product. In addition, no harmful effects on the nostrils or sinus cavities were caused by any of the components of the present composition. The composition effectively eliminated or masked odors associated with smoking and with eating various foods such as onion, garlic and other spices, and certain liquids, particularly alcoholic beverages, coffee, tea, etc.

EXAMPLE 1

The following formula provides a representative example of a composition prepared according to the present invention.

| | |
|---|---|
| Sodium Chloride | 0.65% |
| Benzalkonium Chloride | 0.002% |
| Thimerosal | 0.001% |
| Eucalyptol | 0.03% |
| Methyl Salicytate | 0.02% |
| Methol | 0.015% |
| Alcohol 0.07% | |
| PEG or Glycerin | Trace (Optional) |
| Sodium Chloride | Base ingredient also acting as a moisturizer |
| Benzalkonium Chloride | Preservative |
| Thimerosal | Preservative |
| Eucalypton | Flavoring Agent, also containing antiseptic effect |
| Methyl Salicytate | Counterirritant, (Local Analgesic containing flavor similar to Wintergreen) |

-continued

| | |
|---|---|
| Methol | Counterirritant |
| Alcohol | Aids in solubility effect of other ingredients also containing antibacterial effect. |

The above listed formula has undergone testing and has proved effective for its stated purpose. The composition was dispensed from a one-half ounce (½ oz.) pump atomizer bottle and was successful in eliminating and/or masking odors which could be considered offensive in certain circumstances or by certain people, i.e. odors from smoking, consuming onions etc.

Based on experiments that have been conducted, the eucalypton, methyl salicylate and menthol can be replaced by other similar acting ingredients to completely change the flavor. The base ingredient, preservative(s) and alcohol percentages will remain relatively constant. The solution of the invention is prepared according to known techniques and excipients, as described in "Remington's Pharmaceutical Sciences handbook," Hack Publ. Co., N.Y., U.S.A.

It should be stated, the compositions of my invention are not limited to the ingredients stated in original application or the CIP formulation. Substitution ingredients are widely available for each of the essential components, as described in Remington's Pharmaceutical Sciences.

The first intrinsic ingredients of my invention are the Antiseptic and Anti-Infective agents. The elimination of certain types of bacteria, which are known to cause offensive odors, will aid in the freshening of the breath and are selected and formulated to produce the results as described.

The second intrinsic ingredient of my invention is the Aromatic Components which aid in the freshening and deodorizing of the nasal and sinus cavities. These ingredients are selected and formulated to produce the results as described in Claim 6.

The third intrinsic ingredient of my invention is the isotonic, aqueous solution acting as an Osmotic Agent. This ingredient is selected and formulated for the isotonic value and fully disclosed in Remington's Pharmaceutical Sciences, 17$^{th}$ edition. This ingredient is selected and formulated to produce the results further described herein.

EXAMPLE 2

The following formula provides a second representative example of An Isotonic, Sterile, Aqueous Solution prepared according to the present invention. In this formula, the function of the ingredients is given under "Application".

| RANGE | INGREDIENT | APPLICATION | PERCENTAGE |
|---|---|---|---|
| 0.1 to 2% | Sodium Chloride | Osmotic Agent | 0.650 |
| 0.1 to 5% | Sodium Borate | Buffering Agent | 0.100 |

-continued

| RANGE | INGREDIENT | APPLICATION | PERCENTAGE |
|---|---|---|---|
| 0.1 to 9% | Alcohol SD | Solubilizing Agent | 0.090 |
| 0.001 to 2% | Edetate Disodium | Preservative | 0.050 |
| 0.1 to 3% | Glycerin | Solubilizing Agent | 0.001 |
| 0.001 to 5% | Polysorbate 80 | Surfactant | 0.045 |
| 0.001 to 5% | Poloxamer 407 | Antiseptic | 0.030 |
| 0.001 to 5% | Domiphen Bromide | Antiseptic | 0.030 |
| 0.001 to 5% | Cetylpyridinium Chloride | Anti-Infective | 0.040 |
| 0.1 to 2% | Sorbitol | Sweetener | 0.002 |
| 0.1 to 2% | Sodium Saccharin | Sweetener | 0.002 |
| 0.1 to 5% | Aromatic Component | Masking Agent | 0.005 |
| | Deionized Water | Solvent (Vehicle) | <100% (W/W %) |

The examples I have given, both in the parent application and the CIP filing are representative of preferred embodiments. However, the range of my invention should not be limited to these examples in terms of ingredients and administration.

Thus, while an embodiment and various modifications thereof of a composition for freshening nostrils and sinus cavities has been described in detail herein, various additional changes and modifications may be made without departing from the scope of the present invention.

I claim:

1. A composition for freshening sinus cavities comprising a carrier means, and a masking agent for concealing or eliminating odors emanating from the sinus cavities, and an antiseptic means wherein said antiseptic means does not include an alcohol.

2. A composition as defined in claim 1 and further including a preservative.

3. A composition as defined in claim 1 and further including a counterirritant.

4. A composition as defined in claim 1 and further including a solubility enhancer.

5. A composition as defined in claim 1 and further including an antiseptic means.

6. A composition for freshening nostrils and sinus cavities comprising a saline solution as a moisturizing base component a flavoring agent for masking or eliminating odors from the sinuses or nostrils, a preservative means for enhancing the shelf life of the composition, a counterirritant for facilitating acceptance of the composition by the nostrils and sinuses, an anti-infective means, wherein said anti-infective means does not include an alcohol and an alcohol for facilitating solubility of the components.

7. A composition as defined in claim 1 and further including an anti-infective means.

* * * * *